United States Patent [19]

Leyva

[11] Patent Number: 5,522,791

[45] Date of Patent: Jun. 4, 1996

[54] APPARATUS FOR RETRACTING AN INCISION AND INFLATING AN ABDOMINAL CAVITY

[76] Inventor: Horacio A. Leyva, P.O. Box 5317, Hialeah, Fla. 33014

[21] Appl. No.: 298,930

[22] Filed: Aug. 31, 1994

[51] Int. Cl.⁶ .......................... A61M 29/00; A61B 17/02
[52] U.S. Cl. ............................................ 600/207; 606/192
[58] Field of Search .................................. 128/20; 606/198, 606/192, 1; 604/174, 167, 26; 600/207

[56] References Cited

U.S. PATENT DOCUMENTS

| | | | |
|---|---|---|---|
| 3,730,645 | 5/1973 | Mashakaro et al. | 604/26 |
| 4,421,107 | 12/1983 | Estes et al. | 128/20 |
| 5,159,921 | 11/1992 | Hoover | 128/20 |
| 5,199,944 | 4/1993 | Cosmescu | 604/26 |
| 5,226,876 | 7/1993 | Filipi et al. | 604/26 |
| 5,299,564 | 4/1994 | Sabatino | 606/198 |

*Primary Examiner*—Michael H. Thaler
*Assistant Examiner*—Scott B. Markow
*Attorney, Agent, or Firm*—Malloy & Malloy

[57] ABSTRACT

An abdominal retractor comprising a deformable annular-shaped member with an opening therethrough, which is structured and dimensioned for retracting a linear incision in the abdomen and forming the surrounding tissue into a generally circular configuration, thereby providing an access opening into the abdominal cavity large enough for a hand. The annular member is also adapted to contact the retracted abdominal tissues so as to provide a sealing engagement therebetween. A collapsible sleeve is joined to the annular member and is disposed for extension exterior to the abdomen. The sleeve is structured to enable an arm member to be sealingly yet movably enclosed therein such that a hand at the end of the arm member can be introduced through the access opening into the abdominal cavity. The retractor further includes means through which the abdominal cavity can be inflated with gas such as carbon dioxide ($CO_2$).

20 Claims, 2 Drawing Sheets

APPARATUS FOR RETRACTING AN INCISION AND INFLATING AN ABDOMINAL CAVITY

FIELD OF THE INVENTION

This invention relates generally to abdominal retractors, and more particularly to a retractor for retracting an abdominal incision and inflating an abdominal cavity during surgical operations such as laparoscopy.

BACKGROUND OF THE INVENTION

During certain modern surgical procedures, such as during a laparoscopy procedure, a surgeon introduces a miniaturized surgical instrument into a patient's abdominal cavity via a very small incision in the patient's abdominal wall. The abdominal cavity is at least partially inflated with a gas, such as carbon dioxide ($CO_2$). The inflated abdominal cavity allows the surgeon to move and manipulate the surgical instrument inside the patient's abdominal cavity to perform required procedures. The surgical instrument normally includes optical sensors to provide the surgeon visual feedback of the patient's internal anatomical structures through the surgical instrument to help guide the surgeon during the operation.

Normally, the surgeon operates the surgical instrument using only the visual feedback through the surgical instrument to position the instrument at a surgical site and to perform the surgical operation within the inflated abdominal cavity. This limited sensory feedback to the surgeon during an operation can pose a significant disadvantage to successfully performing certain types of procedures.

For example, during an intestinal laparoscopy operation the surgeon does not always see the relevant structures of a patient's internal anatomy. Further, the surgeon does not always know in advance the shape, location, and structural features of a patient's relevant internal anatomical structures. The surgeon relies on visual feedback through the laparoscopy instrument to guide the operation on the patient's internal anatomy, whether the relevant anatomical structures are visible or obstructed from view. Unfortunately, important anatomical structures that are not visible from the point of view of the laparoscopy instrument may be unknown to the surgeon during the operation. These unknown structures can significantly affect the success of the surgical procedure.

During surgical procedures that are performed in a patient's inflated abdominal cavity, such as a laparoscopy procedure, the surgeon can benefit from the introduction of his hand, or that of an assistant, into the patient's abdominal cavity. For example, the hand can provide manual tactile exploration and tactile feedback to the surgeon, thereby increasing the surgeon's ability to sense and manipulate a patient's internal anatomical structures. This additional tactile feedback can help guide the surgeon during the surgical procedure in ways that are not possible using only visual feedback through the surgical instrument. For example, where the structural features are unknown to the surgeon in advance of the operation, and are not visible from the point of view of the surgical instrument, the surgeon's tactile feedback provides valuable information to the surgeon which significantly increases the rate of success for the surgical procedures.

Further, the introduction of a hand into the abdominal cavity can provide manual retraction and manual grasping of anatomical structures within the inflated abdominal cavity to facilitate positioning of the surgical instrument. This can provide better viewing through the surgical instrument and can locate and secure the anatomical structures for performing surgical procedures thereon.

Although a surgeon's hands can be a valuable source of tactile sensory perception and manual manipulation of anatomical structures within a patient's abdominal cavity, no known surgical devices or methods allow a surgeon to use manual tactile exploration and manual manipulation inside a patient's abdominal cavity during surgical procedures involving the inflation of a patient's abdominal cavity, such as during laparoscopy. Accordingly, there is a need in the art for a surgical device and method that allows manual tactile exploration, manual retraction, and manual grasping of anatomical structures within a patient's inflated abdominal cavity, such as during a laparoscopy operation.

SUMMARY OF THE INVENTION

According to one embodiment of the present invention, there is provided a retractor arrangement and a method of use thereof. The retractor comprises a deformable annular shaped member that is structured and dimensioned for retracting a linear incision in the abdomen and forming the surrounding tissue into a generally circular configuration, thereby providing an access opening into the abdominal cavity large enough for a hand. The annulus is also adapted to snugly engage the surrounding tissue so as to provide a seal between the annulus and the surrounding tissue. A collapsible sleeve is joined to the annulus and is disposed for extension exterior to the abdomen. The sleeve is structured to enable an arm member, either human or robotic, to be positioned therein such that a hand or end effector at the end of the arm member can be introduced through the access opening into the abdominal cavity. The retractor further includes means through which the abdominal cavity can be inflated with gas such as carbon dioxide ($CO_2$), and means for sealingly securing the end of the sleeve to the arm member so as to create a sealed enclosure extending from the securing means to the abdominal cavity.

BRIEF DESCRIPTION OF THE DRAWINGS

For a fuller understanding of the nature of the present invention, reference should be had to the following detailed description taken in connection with the accompanying drawings in which.

DESCRIPTION OF THE PREFERRED EMBODIMENT

Figure 1:
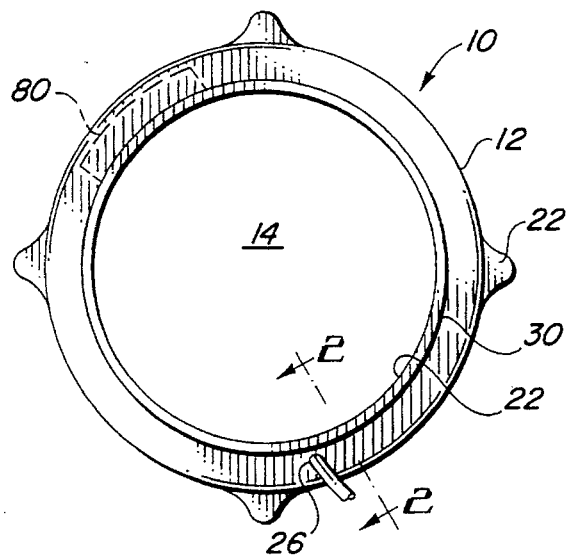
FIG. 1 is a top view of an abdominal retractor in accordance with a first preferred embodiment of the present invention.

Referring to the drawings, FIG. 1 illustrates a first preferred embodiment of the abdominal retractor of the present invention, generally designated as 10. The abdominal retractor 10 comprises a generally ring-shaped member, or annulus 12, preferably constructed of a semi-rigid or resilient material such as rubber, polyurethane, plastic, or a combination thereof, and defining a generally circular opening 14 therethrough. Those skilled in the art will appreciate that the precise size and shape of annulus 12 may be selectively varied, depending upon factors such as the size of the abdominal incision to be retracted and the thickness of the patient's abdominal walls. Annulus 12 should be suitably dimensioned, however, so that the diameter of opening 14 is large enough to allow a human hand or robotic arm end-effector to pass through it. Annulus 12 is capable of being at least partially deformed by the application of a predetermined inwardly directed pressure against the opposite exterior surfaces of its periphery, but is structured to return to its original undeformed shape when the pressure exerted upon it is removed.

Figure 2:
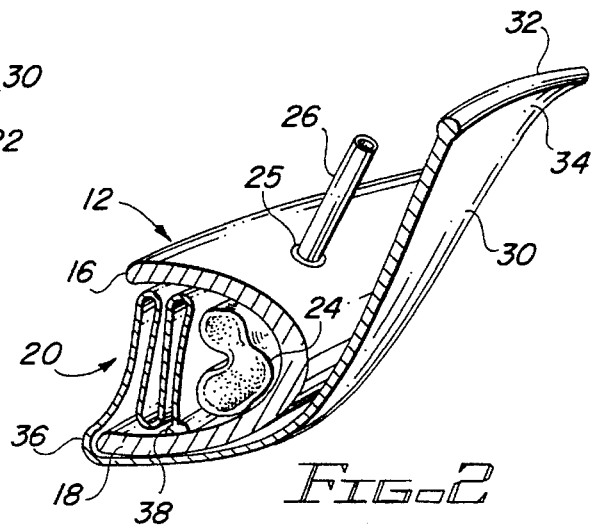
FIG. 2 is a cross-sectional side view of the abdominal retractor of FIG. 1 taken along lines 2—2 of FIG. 1.

As illustrated in FIG. 2, annulus 12 includes an upper wall 16 and a lower wall 18 integrally formed together and defining an annular recess 20 therebetween. Lower wall 18 is preferably configured so that at least one finger member 22 (shown in FIG. 1) protrudes outwardly a predetermined distance from its outer circumference. As described below, finger member 22 is sized to help prevent dislodgement of retractor 10 while it is in use. In the preferred embodiment shown in FIG. 1, four finger members are formed on lower wall 18 and are equally spaced around its outer circumference.

Referring to FIG. 2, retractor 10 also includes an inflatable member 24 having a generally annular shape and removably disposed within recess 20. Inflatable member 24 is structured such that when annulus 12 is fitted within an abdominal incision to provide retraction thereof as described below, the inflation of inflatable member 24 causes it to expand and to provide a seal between its outer surface and the abdominal tissues being retracted. A tubular valve member 26 is joined to inflatable member 24, and preferably is integrally formed therewith, to enable inflation of inflatable member 24 therethrough. Tubular member 26 extends through an aperture 25 in upper wall 16 of annulus 12 and projects outwardly therefrom. Tubular member 26 is adapted for attachment to a syringe or other means of inflation, whereby a liquid or gas can be delivered therethrough with sufficient compression to inflate inflatable member 24. Upon such inflation of inflatable member 24, the compressed gas or liquid can be maintained therein by any suitable type of compression locking arrangement, such as by using a clamp or valve mechanism or by maintaining pressure at a syringe. The pressure exerted by the inflatable member 24, after inflation thereof, will typically be insufficient to cause deformation of the annulus 12 or to cause the annulus 12 to collapse inward and out of sealing engagement with the retracted abdominal tissues. If desired, however, a reinforcement member can be positioned along an inner peripheral zone of the annulus 12. Although not shown in the drawings, a preferred reinforcement member would be in the form of a thin, rigid hoop sized and dimensioned to have substantially the same diameter opening 14 as the annulus 12, and would be positioned along the inner peripheral wall of the annulus to counter act any inward forces exerted by the inflated member 24, and thereby maintain sealing engagement between the annulus 12 and retracted abdominal tissues. While the reinforcement member would preferably be made of stainless steel, it could also be made of another metal or a substantially rigid plastic material.

Figure 3:
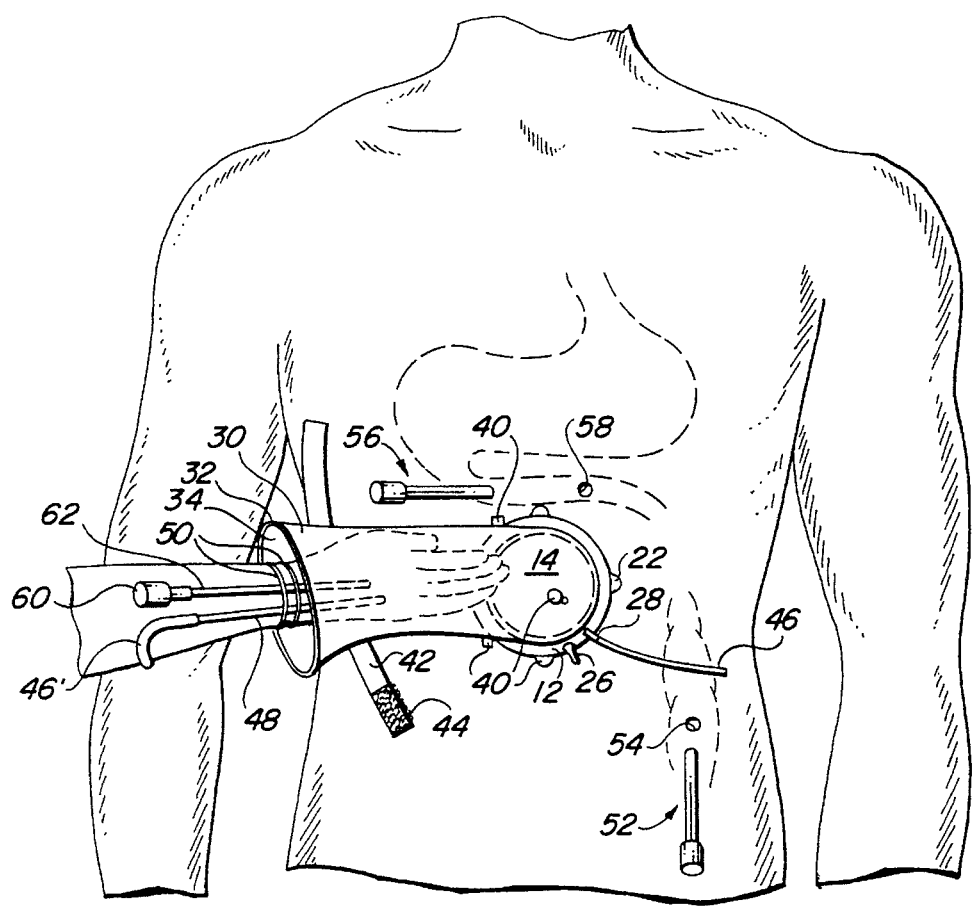
FIG. 3 is a perspective view in partial cutaway of the abdominal retractor of FIG. 1 in use.

As illustrated in FIG. 3, an inflation tube 28 is connected to annulus 12 to provide a first passageway for inflating the abdominal cavity. Inflation tube 28 extends through apertures in upper wall 16 and lower wall 18, and depending upon its positioning may extend through recess 20. Inflation tube 28 includes one segment projecting upwardly from the outer surface of upper wall 16 and another segment projecting downwardly from the outer surface of lower wall 18. Preferably, inflation tube 28 is snugly secured within annulus 12 and may be integrally formed therewith, in order to prevent gas from escaping through the apertures. In the use of the retractor 10 as described below, inflation tube 28 provides a path for $CO_2$ to be introduced directly into the patient's abdominal cavity for inflation thereof.

The retractor 10 of the present invention also includes a collapsible sleeve 30, as shown in FIGS. 2 and 3. Sleeve 30 is preferably constructed of a pliable material such as latex rubber, plastic or vinyl. In the preferred embodiment, a gripping loop 32 is formed around sleeve 30, preferably around the distal end 34 of sleeve 30. Loop 32 is preferably constructed of a resilient flexible material, such as rubber, and is appropriately sized to produce a gripping action about an arm member introduced into sleeve 30, such as a surgeon's forearm. As shown in FIG. 2, the proximal end 36 of sleeve 30 is preferably securely joined to annulus 12 along an inner surface 38 of lower wall 18. Alternatively, proximal end 36 of sleeve 30 may be securely attached to inflatable member 24. Any conventional means of securely attaching rubber, vinyl, or plasticized materials together, such as vulcanization or chemical bonding, can be used to connect sleeve 30 to annulus 12 or inflatable member 24. It will be recognized, however, that sleeve 30 may also be unattached to either annulus 12 or inflatable member 24. For example, proximal end 36 of sleeve 30 may be positioned within recess 20 situated between inflatable member 24 and inner surface 38 of lower wall 18, such that upon inflation of inflatable member 24, proximal end 36 of sleeve 30 will be securely maintained within recess 20 during use of retractor 10. Sleeve 30 preferably is structured and dimensioned for being at least partially folded upon itself and placed within recess 20 for convenient storage prior to use. As shown in FIG. 2, sleeve 30 is securely joined to annulus 12 along inner surface 38 of lower wall 18, and preferably, the sleeve will be unfolded to extend along the outer surface of lower wall 18 and then upwardly along the inner periphery of the annulus and through the retracted incision defined by annulus 12. However, it will be appreciated by those skilled in the art that sleeve 30 could also be unfolded to extend along the outer periphery of annulus 12 without interfering with the sealing engagement between the annulus 12 and the retracted abdominal tissues.

Referring to FIG. 3, sleeve 30 may include at least one inflation valve 40 connected thereto. Inflation valve 40 enables $CO_2$ to be introduced into the patient's abdominal cavity indirectly by passage of the gas through sleeve 30. Regardless of whether $CO_2$ is introduced into the abdominal cavity directly through inflation tube 28 or indirectly through inflation valve 40, the $CO_2$ can be maintained within the abdominal cavity and sleeve 30 only when sleeve 30 is sealingly secured to an arm member by means of loop 32 or other suitable securing means. Such other securing means may comprise a fastening strap or belt 42 that is structured and dimensioned to tightly surround distal end 34 of sleeve 30 so as to provide sealing engagement between the arm member within sleeve 30 and distal end 34. Fastening strap 42 preferably includes hook and loop material 44 at its opposite ends to provide a releasable means of secure engagement, but it will be appreciated that strap 42 may include any suitable structure to provide secure attachment of its opposite ends. Although strap 42 is preferably fixedly attached to the outer surface of distal end 34 of sleeve 30, strap 42 may also be separate and detached from sleeve 30 and function just as effectively. It will be appreciated by those skilled in the art that a surgical glove can be operably and sealingly connected to the sleeve 30 to perform this same function.

While labelled as inflation valves above, the valve mechanisms 40 are suitable for being used to fulfill another purpose. Namely, valves 40 can also be used to introduce various laparascopic instruments into the abdominal cavity without losing $CO_2$ pressure. In such a case, the valve mechanisms are coupled with a tubular sleeve or port through which the laparascopic instruments will pass. This type of valve mechanism is known in the art and is commonly referred to as an endopath. It will be appreciated by those skilled in the art that various laparascopic instruments, such as staplers, scissors, probes, etc. are typically found at the end of a rod like structure and are operable by way of a handle, as one might aliken to the structure of a gun or rifle. Further, that the rod portion of the instrument is typically inserted into the tubular sleeve or port located through an opening in the patient to be operated on, and once in position, the handles are manipulated to control the stapler, scissors, etc. at the end of the instrument, inside the patient. With this invention, the rod portion of the instrument could be inserted into tubular sleeve and valve mechanisms 40 provided on the sleeve 30, for introduction of the instrument into the patient by way of the access opening formed by retractor 10, without losing any of the gas used to inflate the abdominal cavity. In this way, it will be readily understood that laparascopic surgery may be performed with fewer incisions into the patient. In addition, because the rod portion of different laparascopic instruments have various diameter sizes, typically 0.5 millimeters to 18 millimeters, the internal diameter of tubular sleeve and valve mechanisms 40 can also vary. For example, as shown in FIG. 3, there are four inflation valves 40, and each could be provided with a tubular sleeve of differently sized internal diameters to accommodate various laparascopic instruments. Alternatively, already known devices could be utilized to reduce the internal diameter of the endopath within valve mechanism 40.

In the use of the retractor 10 during a surgical procedure, sleeve 30 is at least partially extended out from its folded storage position within recess 20 of annulus 12. A linear incision is then made in the patient's abdomen, which incision will have a length less than the diameter of opening 14 of annulus 12, and is at least partly retracted using conventional surgical retractors. The surgeon partially collapses annulus 12 by squeezing its opposite sides, enabling it to be placed within the retracted incision. The deformed annulus 12 is then fitted into the abdominal incision with the abdominal tissues exposed by the incision positioned within recess 20, with finger members 22 disposed underneath the lower surface of the abdominal wall, and with the downwardly projecting portion of inflation tube 28 extending into the abdominal cavity. Once annulus 12 is so positioned within the retracted incision, the conventional surgical retractors are removed and the surgeon releases the pressure upon the sides of annulus 12, allowing it to return to its original undeformed shape. In doing so, annulus 12 is structured to exert an outwardly directed pressure against the abdominal tissues situated within recess 20, effectively retracting the abdominal incision and providing a substantially snug contacting engagement with the surrounding retracted abdominal tissues.

After annulus 12 has returned to its undeformed shape, the surrounding abdominal tissues retracted by annulus 12 are disposed in a generally circular configuration corresponding to opening 14, providing an access opening into the abdominal cavity sized large enough for a human hand, or robotic arm end-effector, to fit through. Tubular valve member 26 is then coupled to a syringe or other pneumatic compression means (not shown), such as a compressor for delivering air or other fluid or gas under pressure into inflatable member 24. After it has been inflated, inflatable member 24 fills any residual spaces or gaps between annulus 12 and the abdominal tissues disposed within recess 20, thereby improving the sealed engagement between annulus 12 and the retracted abdominal tissues. The sealing contact thereby created between annulus 12 and the retracted abdominal tissues allows the abdominal cavity to be inflated with gas by generally preventing leakage of the pressurized gas from the abdominal cavity.

As shown in FIG. 3, a surgeon's hand and at least a portion of the surgeon's arm can be introduced into sleeve 30, with the hand being positioned adjacent annulus 12 and disposed for passage through opening 14 into the patient's abdominal cavity. Sleeve 30 is secured around a portion of the surgeon's arm, such as his forearm, so as to provide a sealing engagement therebetween, either by means of the snug gripping action of loop 32, or by securing fastening strap 42 tightly around distal end 34 of sleeve 30 and the arm therein, or both. Those skilled in the art will appreciate that when sleeve 30 is sealingly secured to the surgeon's arm, a substantially sealed continuous enclosure is created which extends from the surgeon's forearm to the abdominal cavity, by reason of the sealed engagement between annulus 12 and the retracted abdominal tissues, proximal end 36 of sleeve 30 and annulus 12, and distal end 34 of sleeve 30 and the surgeon's forearm. This substantially sealed continuous enclosure enables the abdominal cavity and sleeve 30 disposed exteriorly thereto to be inflated with $CO_2$ during the surgical procedure while preventing leakage of the gas and consequent deflation of the abdominal cavity.

After sleeve 30 has been sealingly secured to the surgeon's arm, the patient's abdominal cavity can be inflated, either directly through inflation tube 28 or indirectly through inflation valve 40. When inflation tube 28 is used, a coupling tube 46 is also preferably used to connect a pneumatic compression means such as a compressor to inflation tube 28. The patient's abdominal cavity may also be inflated through a mobile inflation tube 48 connected to the surgeon's arm, which can be carried through opening 14 into the abdominal cavity. Mobile tube 48 preferably has a semi-rigid structure that generally maintains its shape even under significant pressure, and may be secured to the surgeon's wrist by means of one or more fastening bands 50. When the surgeon's arm is sealingly yet movably enclosed within sleeve 30, mobile tube 48 provides yet another passageway for inflating the patient's abdominal cavity. As with inflation tube 28, a coupling tube 46' is preferably used to couple mobile tube 48 to a pneumatic compression means such as a compressor for delivering gas to inflate the abdominal cavity. It will be recognized that after the patient's abdominal cavity has been inflated with gas under pressure, finger members 22 underlying the abdominal wall serve to prevent dislodgement of annulus 12 that might otherwise result from the outwardly directed pressure of the gas within the abdominal cavity.

Referring to FIG. 3, a first laparoscopy instrument 52 is shown located about a first region of the patient's abdomen cavity and disposed for insertion through a first small opening 54 in the patient's abdomen. The first small opening 54 is generally in the vicinity of the patient's intestines, and enables a surgical procedure to be performed on the intestines by passage of laparoscopy instrument 52 through opening 54. By way of further example, a second type of laparoscopy operation may be performed through a second opening 58 in the abdominal wall located about a different region of the patient's abdomen, utilizing laparoscopy instrument 56. After the surgeon's arm has been sealingly enclosed within sleeve 30 and abdominal cavity and sleeve 30 have been inflated as described above, the surgeon's hand can be introduced into the inflated abdominal cavity during the laparoscopy procedure. The surgeon's hand is able to perform manual tactile exploration, manual retraction, and manual grasping of anatomical organs within the patient's abdominal cavity to assist in the surgical procedure. It will also be recognized that the surgeon's hand can be used to remove surgical specimens or parts of organs from the abdominal cavity through retractor 10 in good condition for pathological studies. Those skilled in the art will appreciate that instead of using a human arm and hand with the retractor 10, a robotic arm and end effector may be utilized in conjunction with the present invention. Instead of being secured to a human arm as described above, sleeve 30 may be sealingly fastened to the robotic arm to provide the sealed enclosure within which the robotic end-effector can move through opening 14 in annulus 12 to gain access to patient's inflated abdominal cavity.

FIG. 3 also illustrates other means for performing a laparoscopic operation within a patient's abdominal cavity. In this example, laparoscopy instrument 60 may be introduced into the patient's abdominal cavity through opening 14 of annulus 12, by attaching instrument 60 to the surgeon's arm by at least one fastening band 50. The laparoscopy instrument 60 may include a sealed tube structure 62 that is secured by bands 50 to the surgeon's wrist. After the surgeon's hand has been introduced into the inflated abdominal cavity, laparoscopy instrument 60 can be extended through the sealed tube structure 62 to position its distal end at a surgical site within the patient's inflated abdominal cavity. Alternatively, as has been described, laparascopic instruments can be passed into the abdominal cavity by way of valve mechanisms 40 shown on sleeve 30.

Figure 4:
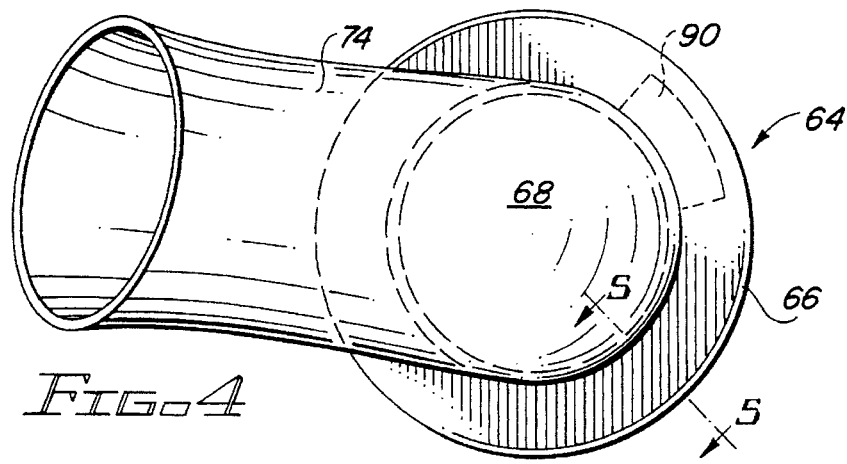
FIG. 4 is a top view of an abdominal retractor in accordance with a second preferred embodiment of the present invention.
Figure 5:
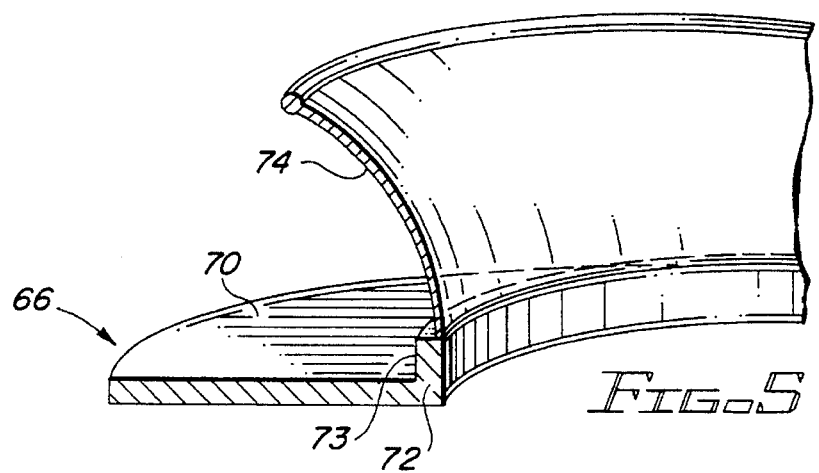
FIG. 5 is a cross-sectional side view of the abdominal retractor of FIG. 4 taken along lines 5—5 of FIG. 4.
Figure 6:
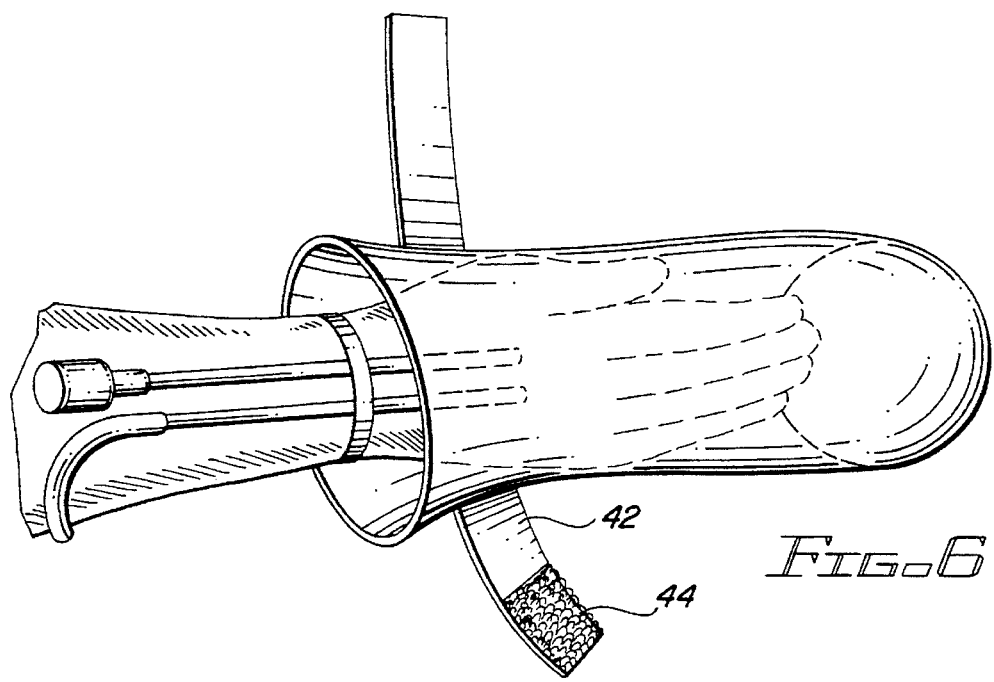
FIG. 6 is a perspective view showing a fastening strap used to secure the sleeve to the arm member.

A second preferred embodiment of the retractor of the present invention is illustrated in FIG. 4. The retractor 64 comprises a substantially ring-like member or annulus 66, preferably constructed of a semi-rigid and resilient material, such as rubber, polyurethane, or plastic, or a combination thereof, and defining a generally circular opening 68 therethrough. As illustrated in FIG. 5, annulus 66 includes a generally flat annular base 70 preferably having a smooth relatively wide surface for confronting engagement against the inner surface of an abdominal wall. Annulus 66 also includes a circumferential sidewall 72 joined perpendicularly to the inner periphery of annular base 70 and preferably integrally formed therewith. Similar to the first preferred embodiment of the present invention, the precise size and shape of annulus 66, including circumferential sidewall 72, may be selectively varied, depending upon factors such as the size of the abdominal incision to be retracted and the thickness of the patient's abdominal walls. Annulus 66 should be suitably dimensioned, however, so that the diameter of opening 68 is large enough to allow a human hand or robotic end-effector to fit through it. Also similar to the first preferred embodiment of the present invention, annulus 66 is capable of being at least partially deformed by the application of a predetermined inwardly directed pressure against the opposite exterior surfaces of its periphery, but is structured to return to its original undeformed shape when the pressure exerted upon it is removed. Retractor 64 preferably includes an inflation tube (not shown) structured and disposed therein identically to inflation tube 28 of the first preferred embodiment, as well as a sleeve 74 structured identically to sleeve 30 of the first preferred embodiment. Because of the different configurations of annulus 12 and annulus 66, however, the proximal end of sleeve 74 will be fixedly secured either to the top edge or outside surface of circumferential sidewall 72, or to annular base 70 at its juncture with circumferential sidewall 72, by any suitable means of fixed securement such as chemical bonding.

Retractor 64 is used in the same manner as retractor 10, except that annulus 66 fits within the retracted abdominal incision differently. The surgeon places the partly collapsed annulus 66 within the abdominal incision with the outer surface 73 of circumferential sidewall 72 disposed in contacting engagement with tissues exposed by the incision and annular base 70 positioned underneath the abdominal wall adjacent the incision. Once annulus 66 is so positioned within the retracted incision, the conventional surgical retractors are removed and the surgeon releases the pressure on the sides of annulus 66, allowing it to return to its original undeformed shape. In doing so, annulus 66 is structured so that circumferential sidewall 72 exerts an outwardly directed pressure against the abdominal tissues exposed by the incision, effectively retracting the abdominal incision and providing a substantially sealing engagement with the retracted abdominal tissues. The top surface of annular base 70 sealingly adheres to the lower surface of the abdominal wall by intra-abdominal pressure, as well as by pressure exerted upon it when the abdominal cavity is inflated with $CO_2$. As with the first preferred embodiment of the present invention, after annulus 66 has returned to its undeformed shape, the surrounding abdominal tissues retracted by annulus 66 are disposed in a generally circular configuration corresponding to opening 68, providing an access opening into the abdominal cavity sized large enough for a human hand, or robotic arm end-effector, to fit through. The sealing engagement created between the top surface of annular base 70 and the inner abdominal wall, and circumferential sidewall 72 and the tissues exposed by the abdominal incision, enables inflation of the abdominal cavity while preventing the escape of the pressurized gas therefrom.

It will be appreciated that retractor 64, as well as retractor 10 of the first embodiment, may include a means for lighting the abdominal cavity 80 and 90. For example, a light source 90 could be operably connected to retractor 64 on the lower surface of annular base 70, and on retractor 10 of the first embodiment, on the lower wall 18, with the light source 80 being appropriately sized and dimensioned to provide lighting of the abdominal cavity. In the preferred embodiment, the light source 80 and 90 provided on retractors 64, 10 would also be readily deformable as is the retractor 10, 64 to which it is operably connected. For example, the light source 80 and 90 may comprise small, interconnected segments lining the periphery along the lower surface of the annulus which can be selectively illuminated. Those skilled in the art will also appreciate that various fiber optic cables could also be utilized in connection with the retractors for providing a light source.

It is therefore seen that the present invention provides a number of significant advantages. First, the abdominal retractor allows a surgeon's hand to be introduced into a patient's sealed and inflated abdominal cavity during a surgical procedure such as laparoscopy, which cannot presently be accomplished with any conventional surgical procedures or instrumentation. The surgeon's use of his hand can reduce the time required to perform the surgical procedure while increasing the reliability thereof, thereby reducing the potential trauma to the patient caused by lengthy operative duration while reducing the time based costs of surgery. The retractor permits access to the patient's entire abdominal cavity by a small infra-umbilical incision, which is the best tolerated incision in the abdominal wall because there is minimal interference with respiratory action and less association with respiratory complications. Additionally, by utilizing manual tactile exploration, manual retraction, and manual grasping within the patient's inflated abdominal cavity to assist in the surgical procedure the present invention significantly enhances the sensory feed back to the surgeon over the conventional visual-only approach such as used in laparoscopy procedures. This advantage of tactile feedback during procedures within the patient's abdominal cavity can not be overstated. It can make surgery faster, higher quality, and more reliable than conventional instrumentation and techniques provided in the past. As has been described, this invention makes it possible, if desired, to the gas, e.g., carbon dioxide, for inflating the abdominal cavity can be introduced through the single abdominal incision for the abdominal retractors 10, 64. In addition, all surgical instruments, including tube, and hand may pass through a single incision, which reduces greatly the incisional pain for the patient versus having multiple incisions. By inflating the patient's abdominal cavity through the single retracted abdominal incision the surgeon does not need to puncture the patient's abdomen at a second location to inflate the cavity and by performing the laparoscopic surgery with instruments passed through the single incision, the surgeon may not need to puncture the patient at another location. This reduces greatly the incisional pain for the patient, which also tends to interfere with post operational respiratory functioning and recovery.

While this invention has been shown and described in what is considered to be a practical and preferred embodiment, it is recognized that departures may be made within the spirit and scope of this invention which should, therefore, not be limited except as set forth in the claims which follow and within the doctrine of equivalents.

Now that the invention has been described,
What is claimed is:

1. An abdominal retractor to be inserted into an incision made in a patient's abdomen, said retractor comprising:

(A) a resilient deformable generally annular shaped member, said annular member including an upper wall and a lower wall defining a generally annular recessed channel therebetween, said recessed channel being of sufficient size so as to engage abdominal tissues about the incision into said recessed channel in sandwiching relation between the upper and lower walls of said annular member, said annular member defining an access opening about the incision sized large enough for an arm member to pass therethrough into an abdominal cavity;

(B) an inflatable member disposed within said recessed channel of said annular member, said inflatable member being structured and disposed to expand upon inflation so that an inner surface of said inflatable member sealingly engages said annular member and an outer surface of said inflatable member sealingly engages the abdominal tissues;

(C) a sleeve having a proximal end joined to said annular member in surrounding fashion and adapted to extend exteriorly from the abdomen to form a cylindrical shaped passageway for introduction therethrough of the arm member; and (D) means for tightly securing said sleeve to the arm member so as to create a seal therebetween.

2. A retractor as recited in claim 1 further comprising an inflation tube operably connected to said annular member, said inflation tube including means for delivering gas into said abdominal cavity.

3. A retractor as recited in claim 1, further comprising an inflation valve operably connected to said sleeve, said inflation valve providing means for delivering gas into said sleeve and abdominal cavity.

4. A retractor as recited in claim 1 further comprising at least one finger extension projecting outwardly from said lower wall of said annular member, said at least one finger extension being structured and disposed for preventing said annular member from being disengaged from said abdominal tissues.

5. A retractor as recited in claim 1 further comprising tubular means operably connected to said inflatable member and structured and disposed for inflating said inflatable member.

6. A retractor as recited in claim 5 wherein said annular member includes an aperture formed in said upper wall and said tubular means further comprising a tubular member having a first end, a second end, and a middle section, said first end being positioned exterior to said upper wall of said annular member, said middle section passing through said aperture in said annular member and said second end being operably connected to said inflatable member.

7. A retractor as recited in claim 6 wherein said first end of said tubular member is structured and disposed to be operably connected to an inflation means.

8. A retractor as recited in claim 1 wherein said upper wall includes an aperture therein and an inflation tube passes through said aperture.

9. A retractor as recited in claim 1 wherein said means for securing said sleeve to said arm member comprise a fastening strap.

10. A retractor as recited in claim 1 wherein said means for securing said sleeve to said arm member comprise a gripping loop at a distal end of said sleeve.

11. A retractor as recited in claim 1 wherein said lower wall comprises a generally flat annular base and said recessed channel including a circumferential side wall operably joined in a substantially perpendicular orientation to said base for directing an outwardly pressure against the abdominal tissues surrounding said incision.

12. A retractor as recited in claim 11 wherein said flat annular base further comprises a smooth relatively wide surface area for adhering against an undersurface of the abdomen wall surrounding said incision for providing a substantially sealing engagement between said smooth relatively wide surface area and the abdomen wall.

13. A retractor as recited in claim 12 further comprising an inflation tube operably connected to said annular member, said inflation tube including means for delivering a gas into said abdominal cavity.

14. A retractor as recited in claim 12, further comprising an inflation valve operably connected to said sleeve, said inflation valve providing means for delivering a gas into said sleeve and abdominal cavity.

15. A retractor as recited in claim 1 further comprising a means for lighting the abdominal cavity, said means being partially deformable.

16. A retractor as recited in claim 1, wherein the arm member is a surgical instrument such as a robotic end effector.

17. A retractor as recited in claim 1, wherein the arm member is a human hand.

18. A method for retracting an abdominal incision comprising the steps of:
provewing an abdominal retractor as recited in claim 1, comprising said deformable, resilient, generally annularly shaped member;
deforming said resilient, generally annularly shaped member structured and shaped to engage the tissues surrounding the abdominal incision;
inserting said deformed annular shaped member into said incision;
allowing said annular member to return to an original, undeformed shape wherein the tissues surrounding said incision are retracted so as to define an access opening sized large enough for the arm member to pass therethrough into the abdominal cavity, and
inflating said inflatable member to provide a seal between said annular member and said tissues surrounding said incision.

19. The method of claim 18 further comprising the steps of: providing a flexible sleeve connected to said annular member;
inserting, after forming said seal between said annular member and the tissues surrounding the incision, said arm member into said flexible sleeve and through said access opening, said sleeve operably and sealingly connected to said annular member, and
fastening said sleeve to said arm member with said securing means to provide a sealed enclosure about said arm member.

20. The method of claim 19 further comprising the steps of: providing an inflation tube for inflating the abdominal cavity; inflating the abdominal cavity, after providing a sealed enclosure about the arm member, by inserting said inflation tube through said sleeve to provide an inflation path into the abdominal cavity to inflate the abdominal cavity.

* * * * *